Nov. 13, 1973
Plant Pat. 3,409
W. H. JESSEL, JR., ET AL
CHRYSANTHEMUM PLANT
Filed June 15, 1971
3 Sheets-Sheet 1
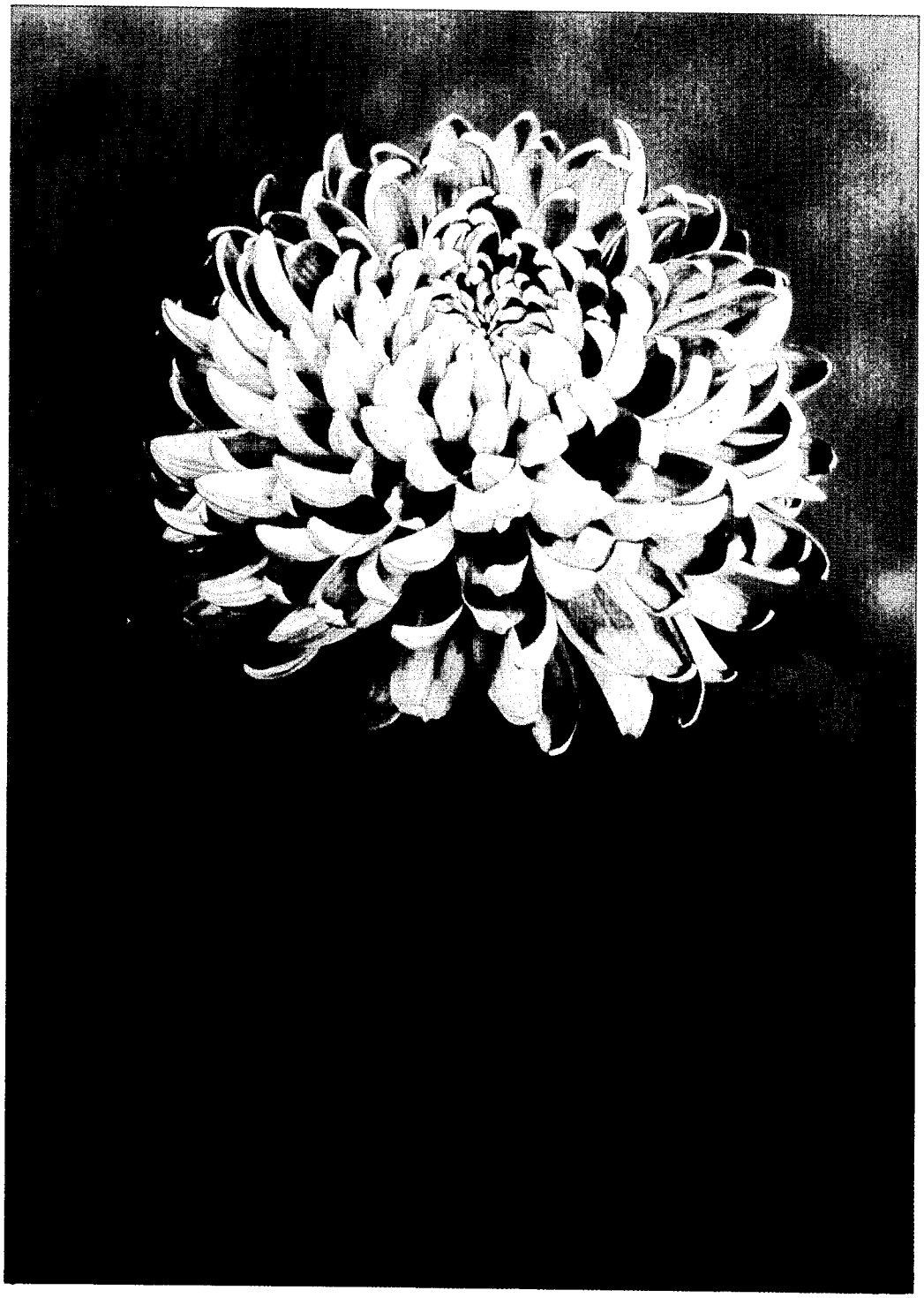

CHRYSANTHEMUM PLANT
Filed June 15, 1971 3 Sheets-Sheet 2
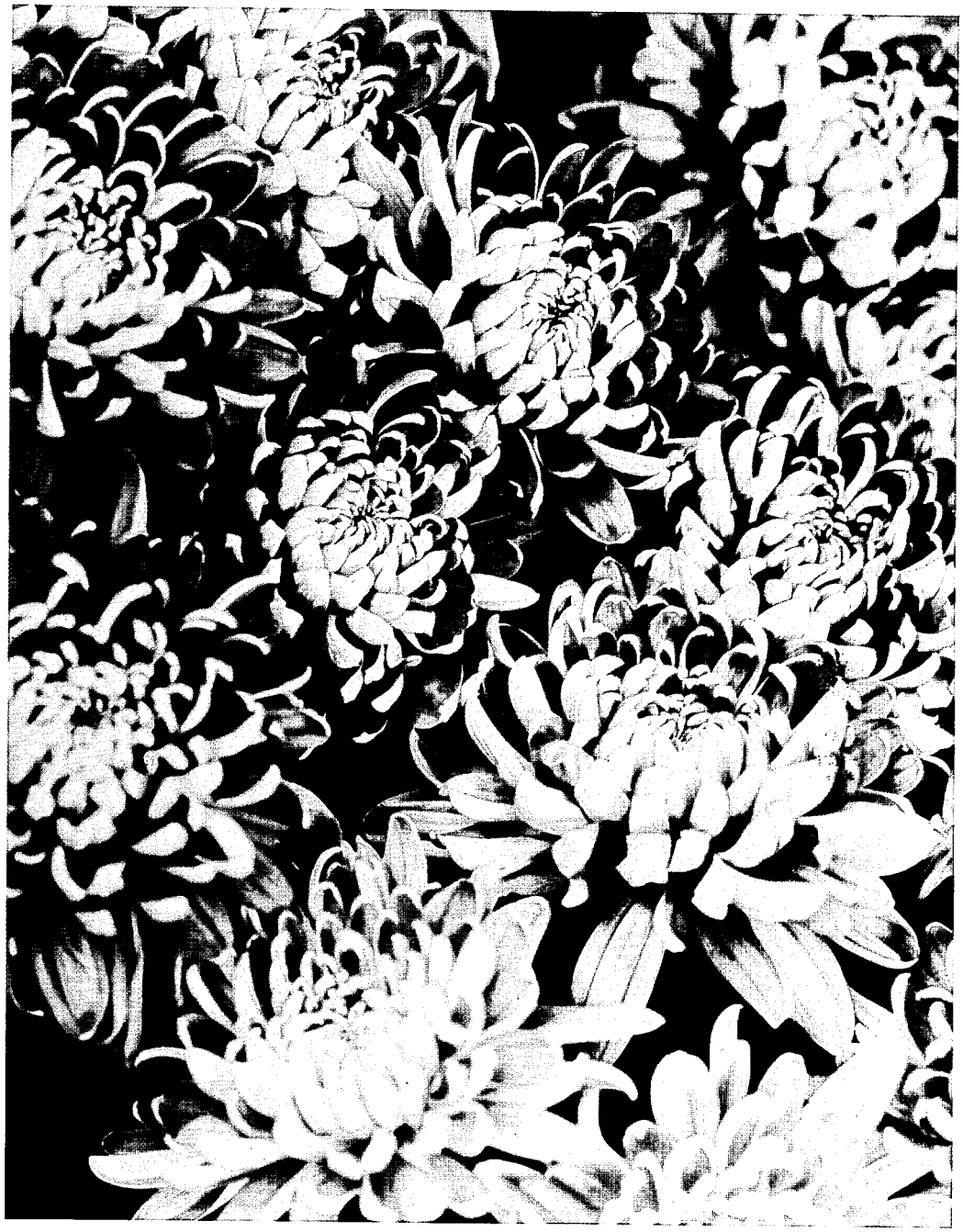

Nov. 13, 1973
W. H. JESSEL, JR., ET AL
Plant Pat. 3,409
CHRYSANTHEMUM PLANT
Filed June 15, 1971
3 Sheets-Sheet 3
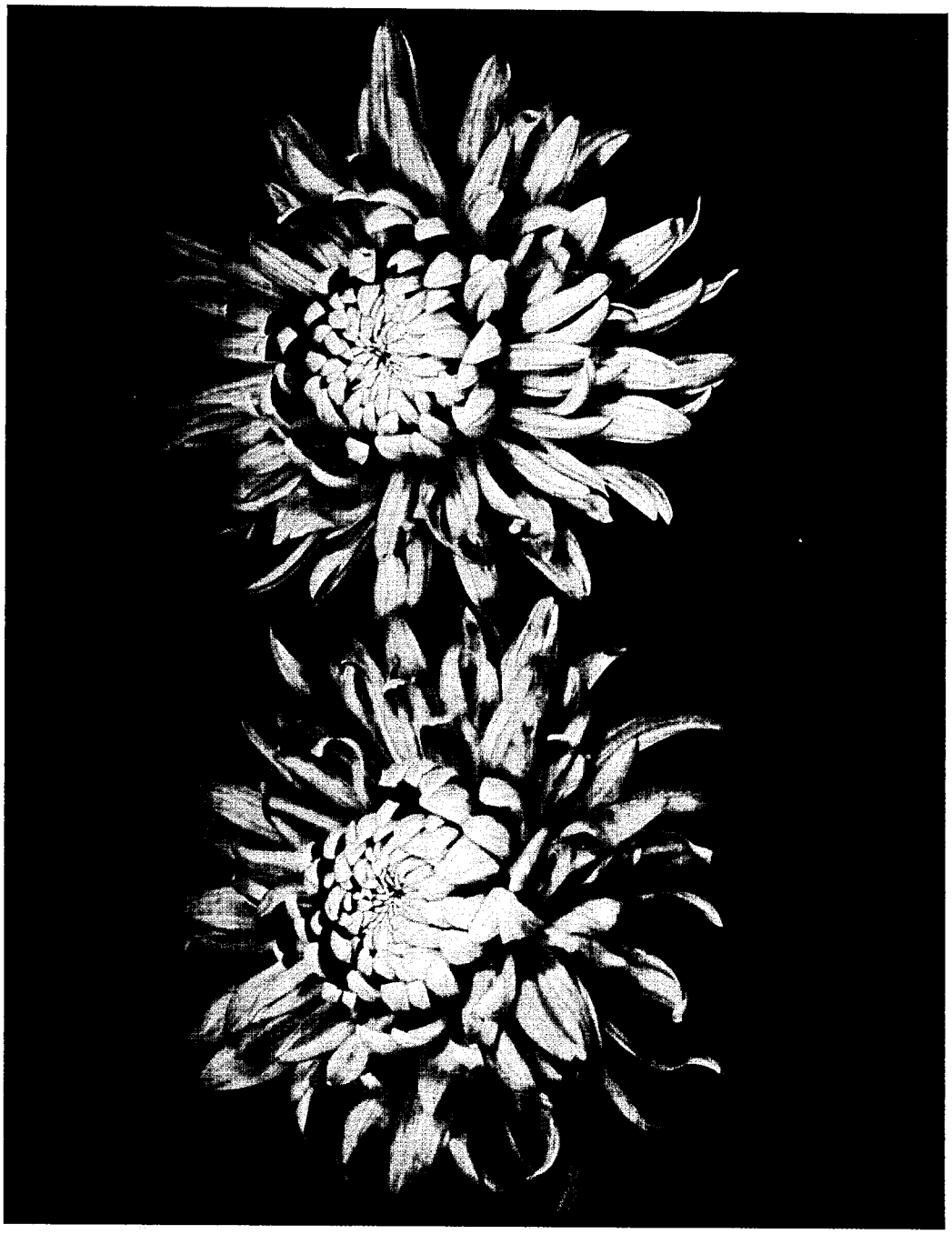

United States Patent Office

Plant Pat. 3,409
Patented Nov. 13, 1973

3,409
CHRYSANTHEMUM PLANT

Walter H. Jessel, Jr., Doylestown, and William E. Duffett, Akron, Ohio, assignors to Yoder Brothers, Inc., Barberton, Ohio

Filed June 15, 1971, Ser. No. 153,456
Int. Cl. A01h 5/00
U.S. Cl. Plt.—79 1 Claim

The present invention comprises a new and distinct cultivar of chrysanthemum plant which is a sport of the cultivar known as Wildfire, the characteristics of which are disclosed and illustrated in our pending application Ser. No. 93,922, filed Nov. 30, 1970, and assigned to Yoder Brothers, Inc., Barberton, Ohio, assignee herein.

The new cultivar is similar in many respects to Wildfire, having the same characteristics of:

(1) Growth habit.
(2) Flower size.
(3) Flower form.
(4) Nine week response.
(5) Foliage size, color and shape.
(6) Propagation either as a pot mum or standard.

The new cultivar is distinguished from Wildfire by a more intense red color when grown under comparable conditions.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity.

Suggested flowering as a pot mum in the northern and western United States and coastal California is from May through October; Florida, December through April; and in the southern United States, May through November.

The accompanying drawings show the unique characteristics of the new cultivar, with the colors being as true as possible with color illustrations of this type. Sheet 1 comprises a specimen photograph of the new cultivar when grown as a standard cut flower. The photograph was taken in the high light conditions of summer, and it will be noted that the flower color is less intense, the flower more highly crowned, and the petal form more incurved. Sheet 2 comprises a comparison photograph of the new cultivar, which appears on the left, and the parent cultivar Wildfire, which appears on the right. This photograph was taken in the spring and shows the cultivars grown in pot mum form. The color differences are apparent, as well as the more incurved flower form which results under the relatively high light conditions of spring. Sheet 3 also comprises a comparison photograph of the new cultivar, which appears on the left and the parent cultivar Wildfire, which appears on the right. The comparison photograph was taken in late fall and the respective cultivars are illustrated in pot mum form. The color differences will again be apparent, and the more decorative and less incurved flower form, due to the relatively lower light conditions, will be evident.

In the description which follows, color references are made to the Munsell Color Book, 1963 edition, and color comparisons are made with the cultivar Wildfire. Where only a single value or description appears for the new cultivar, the same value or description applies to the parent cultivar Wildfire. It should be noted that difficulties were encountered in determining the exact color values, with the color listed comprising the closest available color keys.

Botanical classification: *Chrysanthemum morifolium*

| | Wild Wind | Wildfire |
|---|---|---|
| Bloom: | | |
| Size | 5¼″ | |
| Fully expanded | 5¾″ | |
| Borne | Singly on disbudded stems | |
| Stems | Strong | |
| Form | Semi-incurved | |
| Permanence | 10–14 days | |
| Color: | | |
| Center of flower | Dark red bronze, 10R3/10 to red bronze, 10R4/8 lightly overlaid on yellow, 5Y8.5/10. Effect is golden red. | Light bronze, 5Y7/8 to golden bronze, 5Y7/10. |
| Base of petals | Dark red bronze, 10R3/10 to dark bronze, 1.25YR4/12 lightly overlaid on yellow, 5Y8.5/10. Effect is orange. | Red bronze, 5R3/8 to light bronze; 2.5Y6/8 over yellow, 5Y8.5/10. |
| Inside of petals | Dark red bronze, 10R3/10 to dark bronze, 1.25YR5/12 heavily overlaid on yellow, 5Y8.5/10. Effect is orange-red. | Do. |
| Reverse of petals | Dark red bronze, 10R3/10 to red bronze, 10R4/8 lightly overlaid on yellow, 5Y8.5/10. Effect is golden-red. | Light bronze, 5Y7/8 to golden bronze, 5Y7/10. |
| Tonality from a distance | Red | Orange bronze. |
| Discoloration | Red bronze | Golden bronze. |
| Petals: | | |
| Texture | Smooth | |
| Appearance and form | Open at base, broad keel, tapering to a hooded point | |
| Arrangement | Composite, whorled on a single receptacle | |
| Persistence | Resist shatter | |
| Fragrance | Typical chrysanthemum | |
| Stamen, anthers | None to 30 | |
| Pollen | None to scant | |
| Arrangement | Clustered in center of flower, if present | |
| Styles | Present both ray and disc florets | |
| Length | Short | |
| Ovaries | At the base of petal attached to receptacle | |

TABLE—Continued

| | Wild Wind | Wildfire |
|---|---|---|
| Plant: | | |
| Form | Herbaceous | |
| Growth: | | |
| (a) Pot mum | Semi-upright | |
| (b) Cut mum | Upright | |
| Height: | | |
| (a) Pot mum | Approximately 11"–13" as a single pinched plant using 9 week Tall treatment timing as outlined in the timetables of Yoder Brothers, Inc., Barberton, Ohio. | |
| (b) Cut mum | Approximately 36" when grown on 13 week crop time with 4 long day weeks. | |
| Spread: | | |
| (a) Pot mum | Approximately 8" as a single pinched plant using 9 week Tall treatment timing as outlined in the Yoder mum timetables. | |
| (b) Cut mum | None | |
| Foliage: | | |
| Top side | Dark green, 10GY3/4 | |
| Size: | | |
| (a) Pot mum | 5¼" long, 2½" wide | |
| (b) Cut mum | 7¼" long, 3¾" wide | |
| Quantity | Numerous | |
| Shape | Spatulate lobed | |
| Texture | Smooth | |
| Ribs and veins | Prominent | |
| Edge | Deeply indented | |
| Serration | Very slight | |
| Underside | Light green, 10GY5/4 | |
| Stipules | Prominent | |

We claim:

1. A new and distinct cultivar of chrysanthemum characterized particularly as to its uniqueness when compared to the parent cultivar Wildfire by its more intense red-bronze color.

No references cited.

ROBERT E. BAGWILL, Primary Examiner